United States Patent [19]

Voelz

[11] Patent Number: 4,779,100
[45] Date of Patent: Oct. 18, 1988

[54] POLYGRAPH WITH CONTROL ADJUSTMENT INDICATOR

[75] Inventor: Michael H. Voelz, Battle Ground, Ind.

[73] Assignee: Lafayette Instrument Co., Inc., Lafayette, Ind.

[21] Appl. No.: 76,324

[22] Filed: Jul. 22, 1987

[51] Int. Cl.$^4$ ............................................. G01D 9/00
[52] U.S. Cl. ............................ 346/33 ME; 128/697; 128/710
[58] Field of Search ............... 346/33 ME, 49, 44, 45, 346/23, 17; 128/697, 710, 670, 671, 668, 687, 688, 677, 680, 696, 695, 731; 324/130, 123

[56] References Cited

U.S. PATENT DOCUMENTS

| | | | |
|---|---|---|---|
| 2,235,894 | 3/1941 | Lee | 128/671 |
| 2,655,425 | 10/1953 | Wood | 128/710 |
| 3,908,641 | 9/1975 | Judson et al. | 128/710 |
| 3,915,156 | 10/1975 | Wastl et al. | 128/688 |
| 4,219,028 | 8/1980 | Lencioni, Jr. | 128/731 |

Primary Examiner—E. A. Goldberg
Assistant Examiner—Huan H. Tran
Attorney, Agent, or Firm—Andrus, Sceales, Starke & Sawall

[57] ABSTRACT

Apparatus for detecting and displaying on a polygraph record chart any change in either the sensitivity or balance control of each polygraph electronic module. The apparatus includes a detector in the form of a differentiator for detecting a change in voltage on the wiper of the sensitivity or balance potentiometer that produces a signal indicative of the voltage change, and a display operatively connected to the detector for displaying a signal indicative of the adjustment of the potentiometer. The record chart display includes circuitry having a monostable multivibrator configured as a non-retriggerable one shot device responsive to the voltage change signal from the detector to provide a single pulse driving signal to a pen driving motor. The circuitry also includes a rectifier circuit in the form of comparators responsive to the voltage change signal for producing a positive trigger signal to the one shot device. The pulse amplitude and width of the waveform on the record chart display may be varied to indicate which polygraph channel and potentiometer was adjusted.

10 Claims, 4 Drawing Sheets

POLYGRAPH WITH CONTROL ADJUSTMENT INDICATOR

BACKGROUND OF THE INVENTION

The present invention relates to apparatus for indicating a change in the control setting of an instrument, and more particularly to apparatus for indicating when an adjustment of the sensitivity and balance controls of a polygraph module has occurred.

Instruments for detecting and measuring physiological changes that accompany emotional stress are well-known under the commonly used term of lie detectors. Such instruments are also often called polygraphs, and generally consist of sensors physically connected to an individual's body for measuring various physiological parameters. Such sensors include a blood pressure cuff, a pair of respiration belts, and skin resistance finger electrodes, all suitably coupled to recording pens traversing a record chart. Examples of such instruments and polygraph measuring systems can be found in the following U.S. patents:

| U.S. Pat. No. | Inventor | Issue Date |
| --- | --- | --- |
| 1,472,016 | Dressler | Oct. 23, 1923 |
| 2,944,542 | Barnette et al | July 12, 1960 |
| 3,850,169 | Gebben et al | Nov. 26, 1974 |
| 3,915,156 | Wastl et al | Oct. 28, 1975 |
| 4,085,740 | Allen, Jr. | Apr. 25, 1978 |
| 4,178,918 | Cornwell | Dec. 18, 1979 |
| 4,442,845 | Stephens | Apr. 17, 1984 |
| 4,520,232 | Wilson | May 28, 1985 |

In a polygraph machine, each of the above-noted physiological changes are typically coupled to recording pens by means of an electronic module that has both a sensitivity and balance (centering) control. Each control may be adjusted as desired by an examiner to change the amplitude and vertical position of the recording pens as they traverse a record chart. Oftentimes, an examiner will make such adjustments while an individual subject is under examination to provide a more accurate indication of the physiological changes occurring in response to any emotional stress developed by the subject.

It is therefore desirable to provide apparatus which may be connected to the polygraph modules that could detect if either the sensitivity or balance (centering) control has been adjusted, and display the detected adjustment on the polygraph record chart in such a way that the display would coincide on the chart, in time, with the moment the adjustment was made by the examiner. The purpose of such apparatus is at least two-fold. First, it would aid an examiner with an indication of where notes should be made on the record in order to describe the adjustment that was made. Secondly, it would prevent a change in balance (centering) or sensitivity from being forgotten by an examiner and being mistaken as a response.

SUMMARY OF THE INVENTION

Apparatus for indicating a change in the control setting of an instrument. The apparatus includes detector means for detecting if an adjustable control has been changed, and display means operably connected to the detector means for displaying a signal indicative of the change or adjustment.

The detector means comprises means for detecting a change in voltage in an adjustment potentiometer, and preferably comprises a differentiator means for producing a signal indicative of the voltage change. The display means includes pulse forming means responsive to the voltage change signal from the detector means to provide a pulse driving signal that may be used, for example, to drive a recording pen on the record chart of a polygraph. Preferably, the pulse forming means comprises a monostable multivibrator configured as a non-retriggerable one-shot device.

The display means may also include rectifier means disposed prior to the pulse forming means and responsive to the voltage change signal for producing a trigger signal to the pulse forming means. Preferably, the rectifier means comprises a comparator means operable to produce a positive trigger signal.

In one application of the present invention, the control adjustment indicator apparatus is designed specifically for use with a polygraph to show when changes were made in the sensitivity and balance (centering) controls of each electronic module. The display comprises a square wave whose pulse height, width and direction may be adjusted on the record chart to indicate which polygraph channel and control potentiometer was adjusted so that the controls of all polygraph channels may be monitored.

In another aspect of the present invention, the control adjustment indicator apparatus may be applicable to any instrument where there is a desire to known when the settings of an adjustable control has been changed. Thus, the control adjustment indicator apparatus disclosed may be applied to any instrument with adjustable control potentiometers, and there may be various displays showing that the adjustment has been changed. For example, for pen writting instruments, a glitch in the record may be displayed. For other instruments, a light may be energized or a written statement on a monitor or screen may appear that the adjustment has been made.

Other features and advantages of the invention will become apparent to those skilled in the art upon reviewing the following detailed description, the drawings, and the appended claims.

BRIEF DESCRIPTION OF THE DRAWINGS

The drawings illustrate the best mode presently contemplated of carrying out the invention.

In the drawings.

DESCRIPTION OF THE PREFERRED EMBODIMENTS

Figure 1:
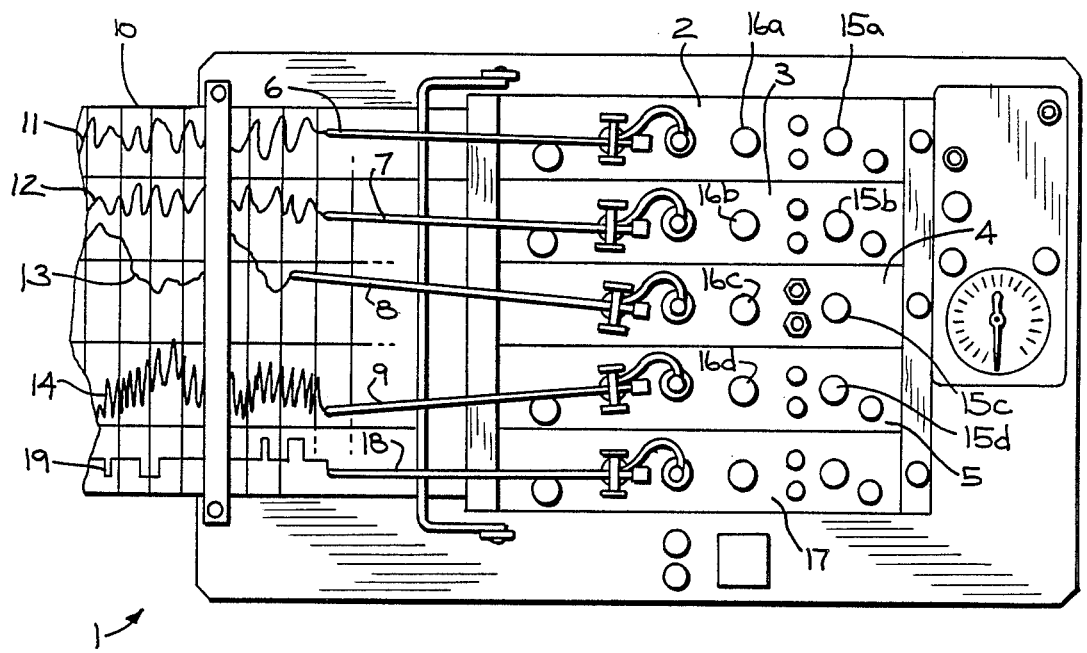
FIG. 1 is a plan view of a polygraph incorporating one embodiment of the control adjustment indicator apparatus of the present invention.

Referring now to the drawings, FIG. 1 illustrates a polygraph generally designated by the numeral 1. Polygraph 1 includes a plurality of electronic modules 2–5 suitable coupled to recording pens 6–9, respectively, which traverse a record chart or strip chart 10. Modules 2–5 are typically employed to detect and measure physiological changes in an individual that accompany emotional stress during a lie detection examination. For example, module 2 may be employed to monitor chest respiration changes in a manner as is shown by waveform 11 on chart 10. Module 3 on the other hand may be employed to detect and record abdominal respiration changes as shown by waveform 12. Module 4 may be employed to measure skin conductance in a manner as shown by waveform 13. Finally, module 5 may be employed to monitor blood pressure changes of the subject as shown by waveform 14.

In order to provide a more accurate indication of the physiological changes occurring in response to emotional stress, an Examiner must be able to adjust the sensitivity or amplitude of waveforms 11–14 as well as control the balance or centering on chart 10 of waveforms 11–14. In order to accomplish this, modules 2–5 each include a sensitivity control 15a–15d as well as a balance or centering control 16a–16d, respectively. Sensitivity controls 15a–15d as well as balance controls 16a–16d each consist of a variable potentiometer comprising an adjustable wiper which moves between extremes of the potentiometer range. Thus, rotation of the appropriate control knob by an examiner will move the wiper of the control potentiometer to change or adjust waveforms 11–14, as desired.

As shown in FIG. 1, polygraph 1 also includes a fifth module 17 suitably coupled to a recordind pen 18 which also traverses chart 10 to produce a waveform 19 which is indicative of an adjustment having been made to one of the sensitivity controls 15a–15d or balance controls 16a–16d. Waveform 19 may show a positive (upward) or negative (downward) squarewave and has a variable pulse amplitude and pulse width to indicate which polygraph channel and adjustment potentiometer was adjusted. The size, shape, and direction of the pulse output of module 17 thus may be adjusted as desired by the Examiner, as will hereinafter be described.

Figure 2:
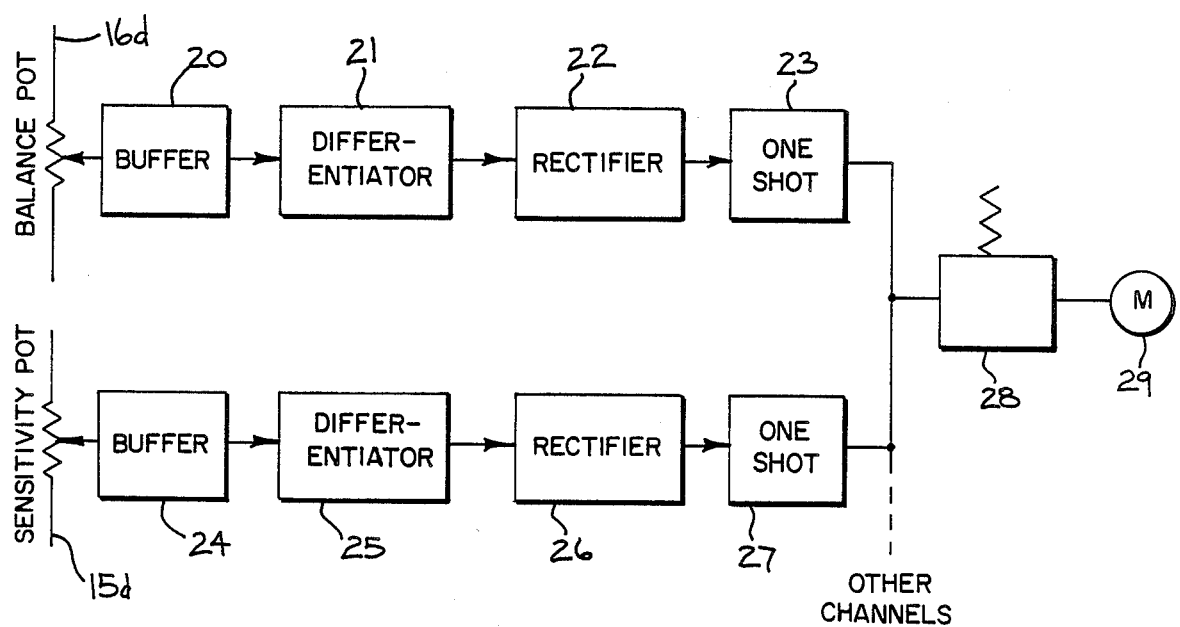
FIG. 2 is a block diagram of the electronic circuitry for the control adjustment indicator apparatus.

Referring now to FIG. 2, there is shown a block diagram of an electronic circuit for module 17 which will detect and display on polygraph chart 10 an adjustment in sensitivity controls 15a–15d or balance controls 16a–16d. Hereinafter, the description will relate to monitoring sensitivity control 15d and balance control 16d of module 5 which monitors and records blood pressure. However, it should be readily apparent to those skilled in the art that any and all of controls 15a–15d and/or 16a–16d may be monitored and displayed on chart 10.

FIG. 2 illustrates that the circuit to detect changes connects to the balance or centering potentiometer 16d, and is isolated or separated from the normal amplifier circuit of polygraph module 5 by means of a buffer amplifier 20. The signal from amplifier 20 is then fed into a differentiator 21. Differentiator 21 detects the changing voltage level on the wiper of the potentiometer of balance control 16d and is configured with gain to provide a spike voltage out if the voltage on the wiper of the balance control potentiometer 16d changes. This spike output voltage will be either positive or negative depending on the direction the knob for balance control 16d is turned by an examiner. The differential output spike is then passed through a rectifier circuit 22 which causes the output spike to always be positive regardless of which direction the balance (centering) control 16d was turned by the examiner. After being rectified, the pulse is fed to the input of a dual precision mono-stable multivibrator 23 which is configured as a non-retriggerable one-shot with its time constant adjustable via the RC time constant circuit thereof. An identical circuit consisting of buffer amplifier 24, differentiator 25, rectifier circuit 26, and multivibrator 27 is also connected to the wiper of the sensitivity control potentiometer as shown in FIG. 2. As also shown in FIG. 2 by the dotted lines, the same circuitry is used for each channel or module 2–4 so that the control adjustment indicator apparatus consists of the same general circuit multiplied times the number of channels to be monitored. The output of multivibrators 23, 27 are then summed into an operational amplifier summer 28, and the output of the summing amplifier 28 drives an amplifier which is used to drive pen motor 29 which in turn drives pen 18 to record waveform 19.

Figure 3:
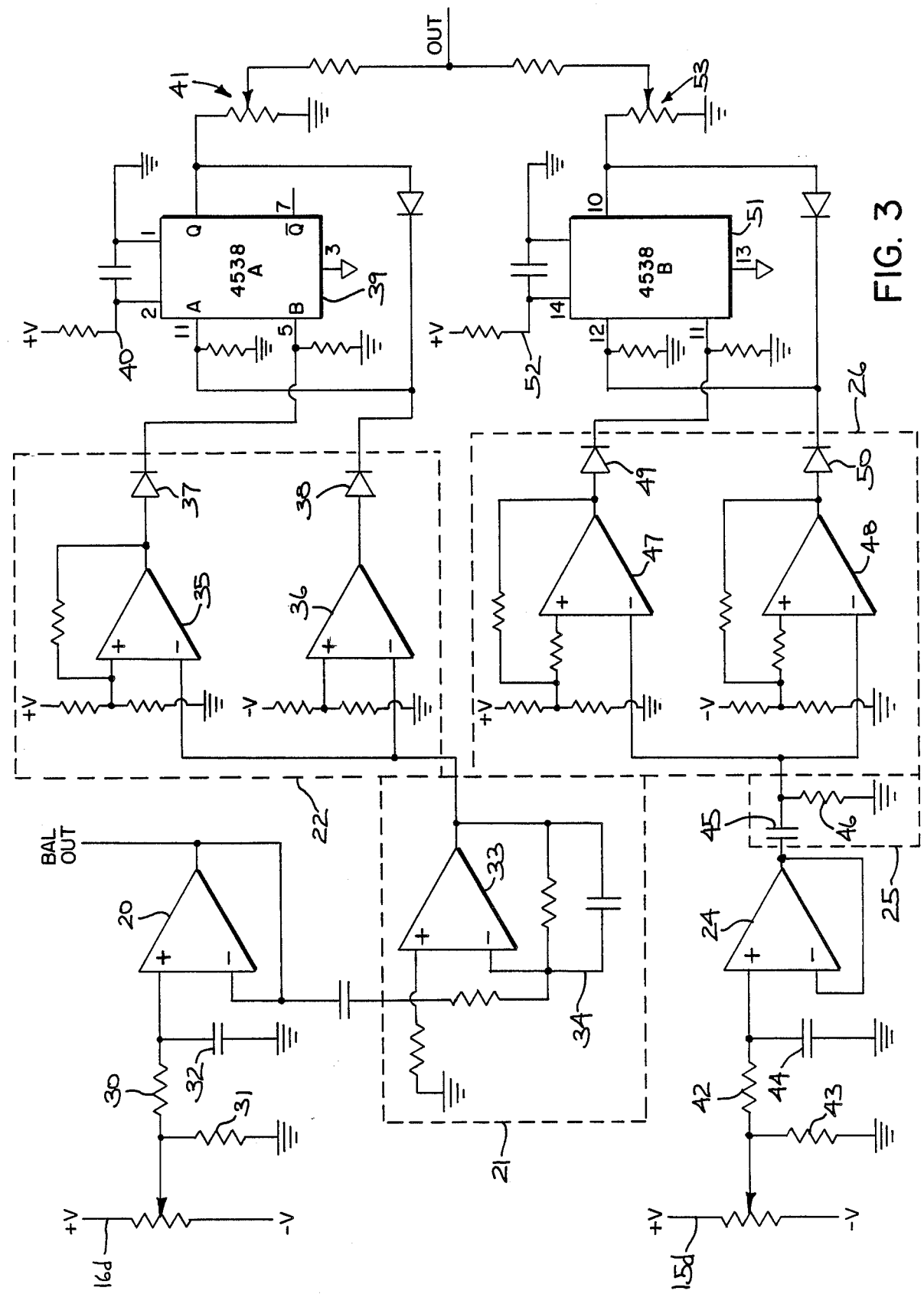
FIG. 3 is a schematic diagram of the electronic circuit for one channel of the polygraph of FIG. 1.

Referring now to FIG. 3, there is shown in detail the preferred circuitry for detecting and displaying when an adjustment of controls 15a–15d and/or 16a–16d occurs. A signal from, for example, balance control potentiometer 16d is first passed through resistors 30, 31 and capacitor 32 to filter and shape the signal to reduce noise. The signal then enters buffer amplifier 20 which isolates the potentiometer from the rest of the circuitry. Buffer 20 sends the balance signal back to a circuit board of module 5 to allow the potentiometer to perform its balancing function and additionally feeds the signal into a differentiator 21. Differentiator 21 detects the changing voltage level on the wiper of balance control potentiometer 16d and is configured with gain to give a spike voltage out which will either be positive or negative depending on the direction the knob of balance potentiometer 16d is turned by an examiner. Differentiator 21 includes amplifier 33 and a feedback circuit 34 consisting of a resistor and capacitor in parallel relationship with one another. The output or voltage change signal from differentiator 21 is fed to rectifier circuit 22 which comprises a pair of comparators 35, 36. Each comparator 35, 36 is biased above zero with comparator 35 biased at a positive voltage while comparator 36 is biased at a negative voltage so that comparators 35, 36 are not triggered by noise on the line so that only a true spike voltage from differentiator 21 will trigger comparators 35, 36. Thus, comparators 35, 36 will give a signal out whenever the signal in on one side thereof changes relative to the signal or the other side thereof. Thus, if the spike voltage change signal is positive, comparator 35 will be triggered and if the spike voltage change signal from differentiator 21 is negative, comparator 36 is set off or triggered. After passing through one of comparators 35, 36 the voltage change signal also passes through a diode 37, 38, respectively, to block any transient negative swings in voltage. The voltage change signal is then fed as a trigger pulse into the input of a dual precision monostable multivibrator 39. Multivibrator 39 is configured as a non-retriggerable one-shot and its time constant is adjustable via the RC time constant circuit 40. One-shot 39 provides a single square wave pulse driving signal each time it receives a trigger pulse from one of comparators 35, 36. The single square wave pulse driving signal output from one-shot 39 then passes through a potentiometer 41 which may be utilized to adjust the amplitude of the driving signal. The driving signal then is fed into pen motor 29 which in turn drives pen 18.

FIG. 3 also illustrates circuitry for detecting and displaying an adjustment of sensitivity control 15d. As shown, the signal from the wiper of control potentiometer 15d which is a ganged potentiometer one stage of which adjusts the sensitivity and another stage of which provides a signal that is first shaped and filtered by resistors 42, 43 and capacitor 44, and is passed through buffer amplifier 24 in the same manner as for balance control 16d. The signal out from buffer 24 is then differentiated by differentiator 25 which includes capacitor 45 and resistor 46. Differentiator 25 is a passive differentiator since the signal from sensitivity control 15d is much greater than the signal from balance control 16d. Thus, an active differentiator such as amplifier 33 is not necessary in connection with the signal from sensitivity control 15d. Again, however, differentiator 25 detects the changing voltage level on the wiper of sensitivity control potentiometer 15d and is configured to give a spike voltage out if the voltage on the wiper of sensitivity control 15d changes. This spike voltage or voltage change signal will be either positive or negative depending on the direction the sensitivity control knob is turned. The voltage change signal from differentiator 25 is then fed into a rectifying circuit 26 comprising a pair of comparators 47, 48 which operate in the previous manner as described with respect to comparators 35, 36 to provide a trigger pulse signal which passes through diodes 49, 50 respectively and is fed into the input of a dual precision monostable multivibrator 51 which is configured as a non-retriggerable one-shot with its time constant adjustable via the RC time constant circuit 52. After receiving a trigger signal from comparator 47 or 48, one-shot 51 fires to provide a single square wave pulse driving signal which is fed through a potentiometer 53, for adjusting its amplitude, and out to pen motor 29 which in turn is coupled to recording pen 18.

Figure 4:
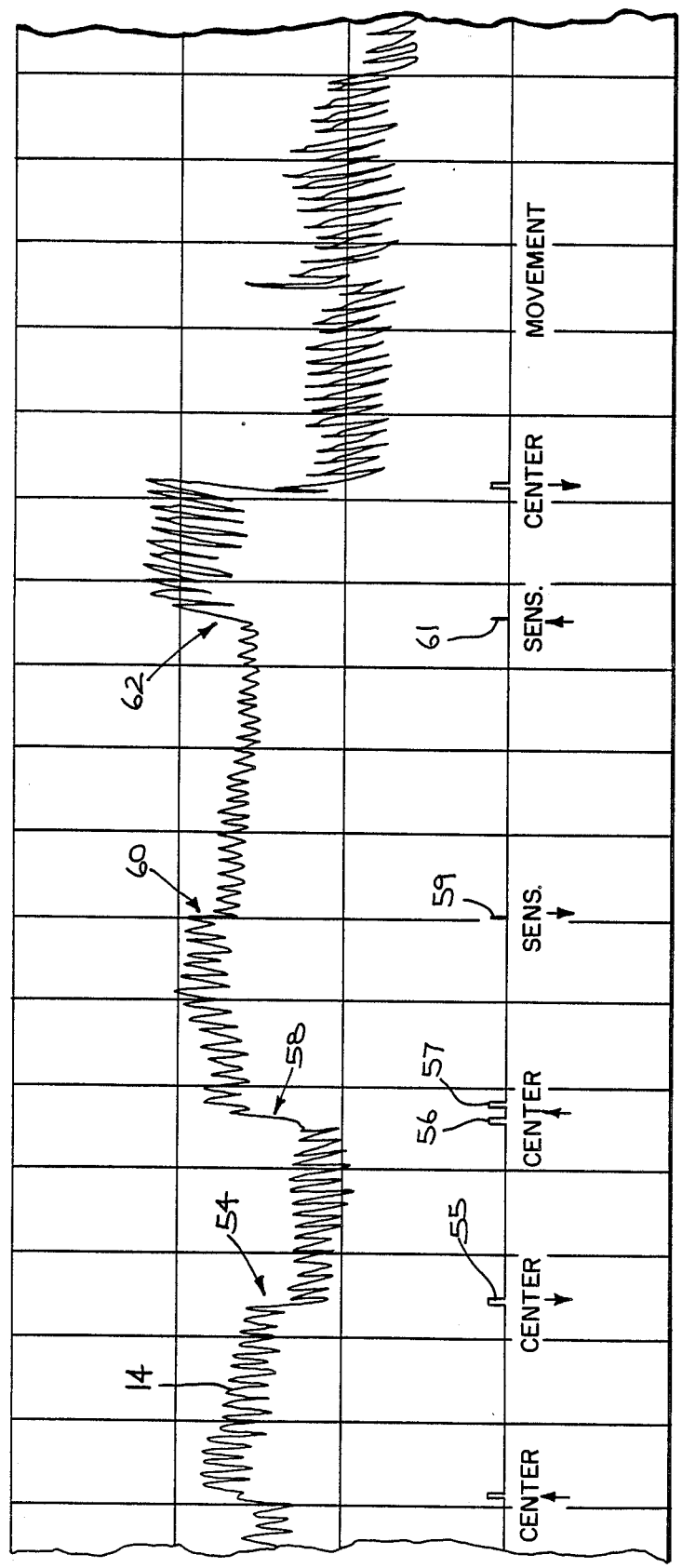
FIG. 4 is a diagram illustrating a record produced by the control adjustment indicator apparatus of FIG. 3.

Referring now to FIG. 4, there is shown a sample record obtained by utilizing the circuitry shown in FIG. 3 in combination with the adjustment of sensitivity control 15d and balance control 16d for cardiomodule 5. As shown, when balance (centering) control 16d is adjusted as at 54 to lower waveform 14 on chart 10, a square wave pulse 55 is generated by module 17 to indicate that control 16d has been adjusted. Likewise, square wave pulses 56, 57 are generated when the centering control 16d is adjusted to move waveform 14 upwardly on chart 10 as at 58. Additionally, FIG. 4 illustrates a pulse 59 generated by module 17 when sensitivity control 15d is adjusted to lower the amplitude of waveform 14 as at 60, and also illustrates another pulse 61 generated when the sensitivity control 15d is adjusted as at 62 to increase the amplitude of waveform 14. It should be noted that pulses 55-57 present a square wave configuration whereas pulses 59 and 61 are essentially spikes on chart 10. This is accomplished by properly adjusting the time constant of multivibrators 23, 27 as desired so that a variable pulse width may be obtained to indicate which polygraph channel and which potentiometer was adjusted. Additionally, it should be noted that by adjusting potentiometers 41 and 53 the amplitude of pulses 55-57, 59 and 61 could be adjusted which may also be utilized if desired to indicate which polygraph channel and potentiometer was adjusted depending upon the number of polygraph channels to be monitored.

Figure 5:
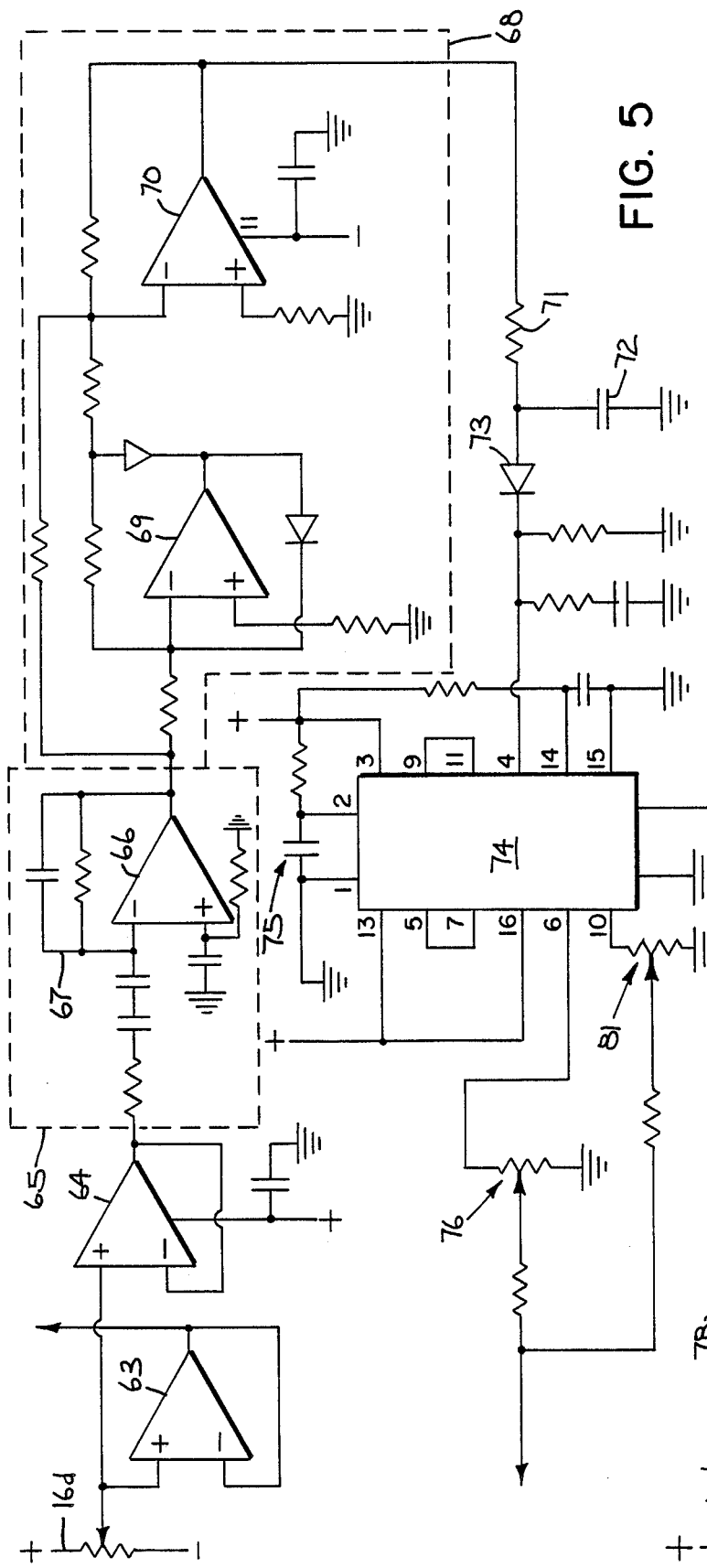
FIG. 5 is a schematic diagram similar to FIG. 3 illustrating a second embodiment of the electronic circuitry for one channel of the polygraph of FIG. 1.
Figure 5:
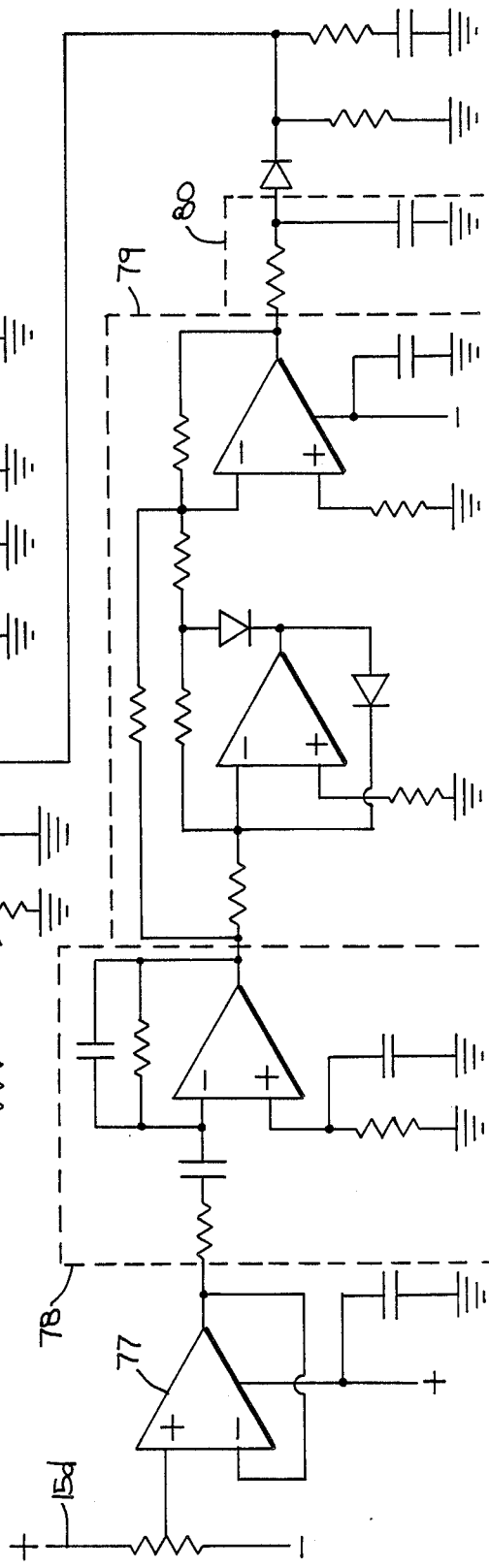

Referring now to FIG. 5, there is illustrated an alternate embodiment for the circuitry shown in FIG. 3 for producing waveform 19 of module 17. As shown, a signal from the wiper of balance control potentiometer 16d is passed through a non-inverting buffer amplifier 63 and is fed to the normal amplifier circuit for module 5 in order to separate the detector circuits from the normal amplifier circuitry of polygraph module 5. The output signal from the wiper of balance control potentiometer 16d is also fed to a non-inverting buffer 64 and from buffer 64 is fed into a differentiator circuit 65. Differentiator circuit 65 detects the changing voltage level on the wiper of balance potentiometer 16d and is configured with gain to give a spike voltage out if the voltage on the wiper of the balance potentiometer 16d changes. This spike voltage or voltage change signal will be either positive or negative depending on the direction the balance control knob is turned by the examiner. Circuit 65 includes an amplifier 66 and a feed back circuit 67 including a resistor and capacitor in parallel relationship with one another. The voltage change signal or spike voltage is then passed through a rectifier circuit which causes the signal to always be positive regardless of which direction the knob of balance (centering) potentiometer 16d is turned by an examiner. As shown in FIG. 5, rectifier circuit 68 includes a pair of amplifiers 69, 70 disposed in series relationship with one another. After being rectified, the pulse is shaped by a resistor 71 and capacitor 72 to filter noise from the pulse, and it then passes through a diode 73 to block any transient negative swings in voltage so that false trigger signals are eliminated. The rectified and shaped signal from differentiator 65 is then fed to the input of a dual precision monostable multivibrator 74 which is configured as a non-retriggerable one-shot with its time constant adjustable via the RC time constant circuit 75. The output or square wave pulse driving signal from multivibrator or one-shot 74 is then fed to a potentiometer 76 in order to adjust its amplitude as desired and then to pen motor 29 which in turn is coupled to recording pen 18.

With respect to sensitivity control potentiometer 15d, FIG. 5 illustrates that the signal from its wiper is first fed into a buffer amplifier 77 to again isolate the circuitry from the remainder of module 5. The output of buffer 77 then feeds into a differentiator circuit 78, a rectifier circuit 79, and a filtering circuit 80 which are identical to those discussed with respect to balance control potentiometer 16d in FIG. 5. The rectified, shaped signal from differentiator 78, which is indicative of a change in the sensitivity control 15d, is then fed to the input of multivibrator 74. The output of multivibrator or one-shot 74 is then passed through a potentiometer 81 which may adjust the amplitude of the single square wave pulse driving signal which thereafter is fed to pen motor 29 and recording pen 18.

The present invention thus provides a control adjustment indicator apparatus for a polygraph machine. However, it should be noted that the apparatus described and illustrated herein is applicable to any instrument where there would be a desire to detect and display when the settings of an adjustment potentiometer control have been changed. The system disclosed and illustrated herein may be applied to any potentiometer and any instrument and there could be any sort of indicator or display that the instrument had been changed. Thus, the present invention is not limited to polygraph machines per se or to pen writing instruments per se.

Various modes of carrying out the invention are contemplated as being within the scope of the following claims particularly pointing out and distinctly claiming the subject matter which is regarded as the invention.

I claim:

1. In a polygraph having sensitivity and balance control means for recording a waveform indicative of a physiological change of an individual, said control means comprises a variable potentiometer including an adjustable wiper, apparatus for indicating when an adjustment of said control means occurs, said apparatus comprising:

detector means for detecting an adjustment of said control means, said detector means comprises differentiator means for detecting a change in voltage on the wiper of the potentiometer and for producing a signal indicative of the voltage change; and display means operably connected to said detector means for displaying a signal indicative of the adjustment of said control means, said display means comprises a record chart, a pen engageable with said record chart, means for driving said pen on said chart, and circuit means including pulse forming means operably connected to said pen driving means and responsive to the voltage change signal from said detector means to provide a single pulse driving signal to said pen driving means.

2. The polygraph of claim 1 wherein said pulse forming means comprises a monostable multivibrator means.

3. The polygraph of claim 2 wherein said multivibrator means is configured as a non-retriggerable one-shot device.

4. The polygraph of claim 1 wherein said circuit means further includes rectifier means disposed prior to said pulse forming means and responsive to said voltage change signal for producing a trigger signal to said pulse forming means.

5. The polygraph of claim 4 wherein said rectifier means comprises comparator means operable to produce a positive trigger signal.

6. Apparatus for indicating a change in the control setting of an instrument, comprising:

detector means for detecting a change in the setting of an adjustable potentiometer of an instrument, said detector means comprises means for detecting a change in voltage in said adjustable potentiometer, and said means for detecting a change in voltage comprises differentiator means for producing a signal indicative of the voltage change; and display means operably connected to said detector means for displaying a signal indicative of the change of said potentiometer, said display means comprises circuit means including pulse forming means responsive to the voltage change signal from said detector means to provide a single pulse driving signal.

7. The apparatus of claim 6 wherein said pulse forming means comprises a monostable multivibrator means.

8. The apparatus of claim 7 wherein said multivibrator means is configured as a non-retriggerable one-shot device.

9. The apparatus of claim 6 wherein said circuit means further includes rectifier means disposed prior to said pulse forming means and responsive to said voltage change signal for producing a trigger signal to said pulse forming means.

10. The apparatus of claim 9 wherein said rectifier means comprises comparator means operable to produce a positive trigger signal.

* * * * *